United States Patent [19]

Grim et al.

[11] Patent Number: 4,964,402
[45] Date of Patent: Oct. 23, 1990

[54] ORTHOPEDIC DEVICE HAVING GEL PAD WITH PHASE CHANGE MATERIAL

[75] Inventors: Tracy E. Grim, Broken Arrow, Okla.; Jeffrey R. Haines, Encino, Calif.

[73] Assignee: Royce Medical Company, Culver City, Calif.

[21] Appl. No.: 233,273

[22] Filed: Aug. 17, 1988

[51] Int. Cl.$^5$ .............................................. A61F 5/00
[52] U.S. Cl. .................................. 128/80 H; 128/402
[58] Field of Search ..................... 128/80 H, 166, 402, 128/400

[56] References Cited

U.S. PATENT DOCUMENTS

| | | | |
|---|---|---|---|
| 3,548,420 | 12/1970 | Spence | 128/DIG. 21 |
| 3,628,537 | 12/1971 | Berndt et al. | |
| 3,663,973 | 5/1972 | Spence | |
| 3,717,145 | 2/1973 | Berndt et al. | |
| 3,780,537 | 12/1973 | Spencer | |
| 3,858,379 | 1/1975 | Graves et al. | |
| 3,885,403 | 5/1975 | Spencer | |
| 3,889,684 | 6/1975 | Lebold | |
| 3,900,035 | 8/1975 | Welch et al. | |
| 4,055,188 | 10/1977 | Pelton | |
| 4,092,982 | 6/1978 | Salem | |
| 4,243,041 | 1/1981 | Paul | |
| 4,280,489 | 7/1981 | Johnson, Jr. | |
| 4,377,160 | 3/1983 | Romaine | |
| 4,504,402 | 3/1985 | Chen | 252/70 |
| 4,572,169 | 2/1986 | Mauldin et al. | |
| 4,587,279 | 5/1986 | Salyer et al. | |
| 4,596,250 | 6/1986 | Beisang | 128/402 |
| 4,617,332 | 10/1986 | Salyer et al. | |
| 4,628,945 | 12/1986 | Johnson, Jr. | 128/89 R |
| 4,671,267 | 6/1987 | Stout | 128/156 |
| 4,708,812 | 11/1987 | Hatfield | 252/70 |
| 4,711,813 | 12/1987 | Salzer | 252/70 |
| 4,756,311 | 7/1988 | Francis, Jr. | |

FOREIGN PATENT DOCUMENTS 823024179 1/1983 European Pat. Off. .
1600505 10/1981 United Kingdom .

OTHER PUBLICATIONS

"Advanced Phase-Change Materials for Passive Solar Storage Applications", by I. O. Salyer, et al., University of Dayton Research Institute, Society of Automotive Engineers, Inc., 1985, pp. 3.699-3.709.

Primary Examiner—Edgar S. Burr
Assistant Examiner—Huong Q. Pham
Attorney, Agent, or Firm—Poms, Smith, Lande & Rose

[57] ABSTRACT

An orthopedic device for treatment of injured joints or limbs having at least one gel pad including at least one phase change material for improving the thermal energy storage capacity of the gel pad. The phase change material included in the gel material inside the gel pad may be encapsulated, formed in pellets, soluble, insoluble, or in any desirable form. The gel pad may be removed from the orthopedic device, heated or cooled, and then used with the device for hot or cold therapy of injured joints or limbs, taking advantage of the increased thermal energy storage capacity of the phase change material. Two different phase change materials may be included in the gel pad, one of which may be used for cold temperature therapy while the other is used for hot temperature therapy. The gel pad may include encapsulated water as a phase change material. In addition, a sheet of encapsulated phase change material may be used inside the gel pad which prevents the phase change material from moving inside the gel pad in order to provide a uniform distribution of phase change material inside the pad, resulting in uniform temperature distribution for hot or cold therapy.

16 Claims, 4 Drawing Sheets

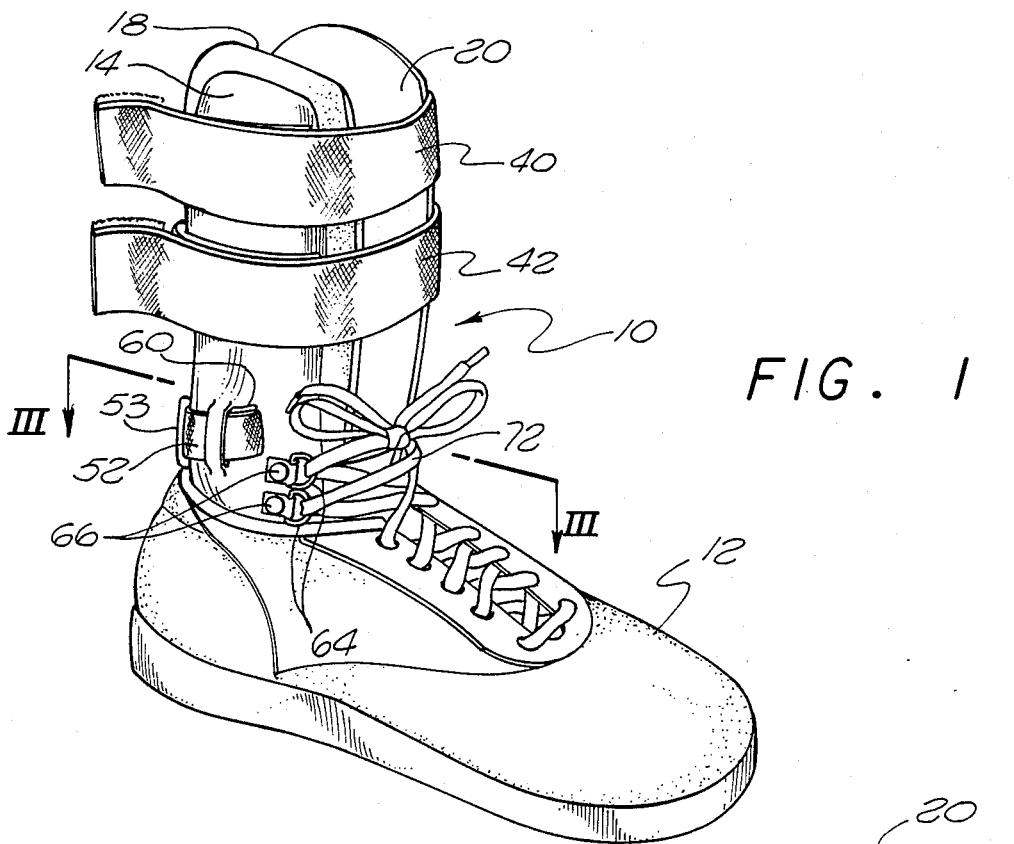
FIG. 1
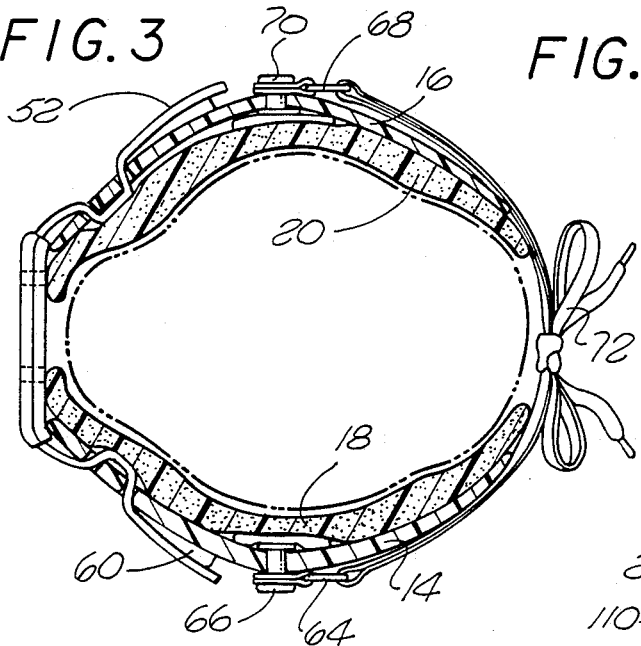
FIG. 3
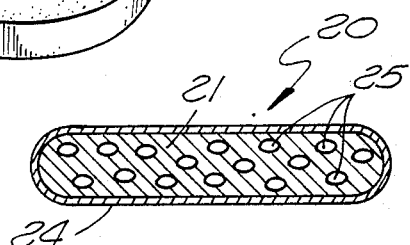
FIG. 4
FIG. 5
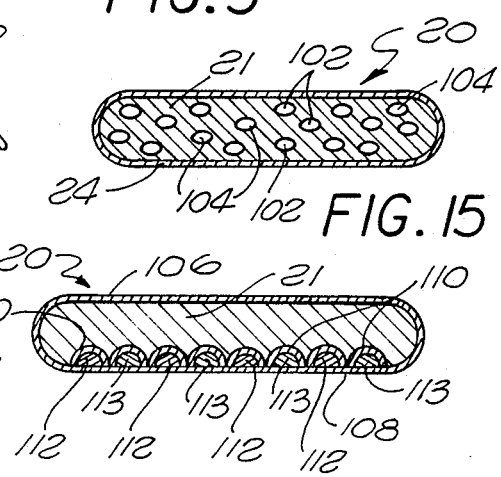
FIG. 15
FIG. 16

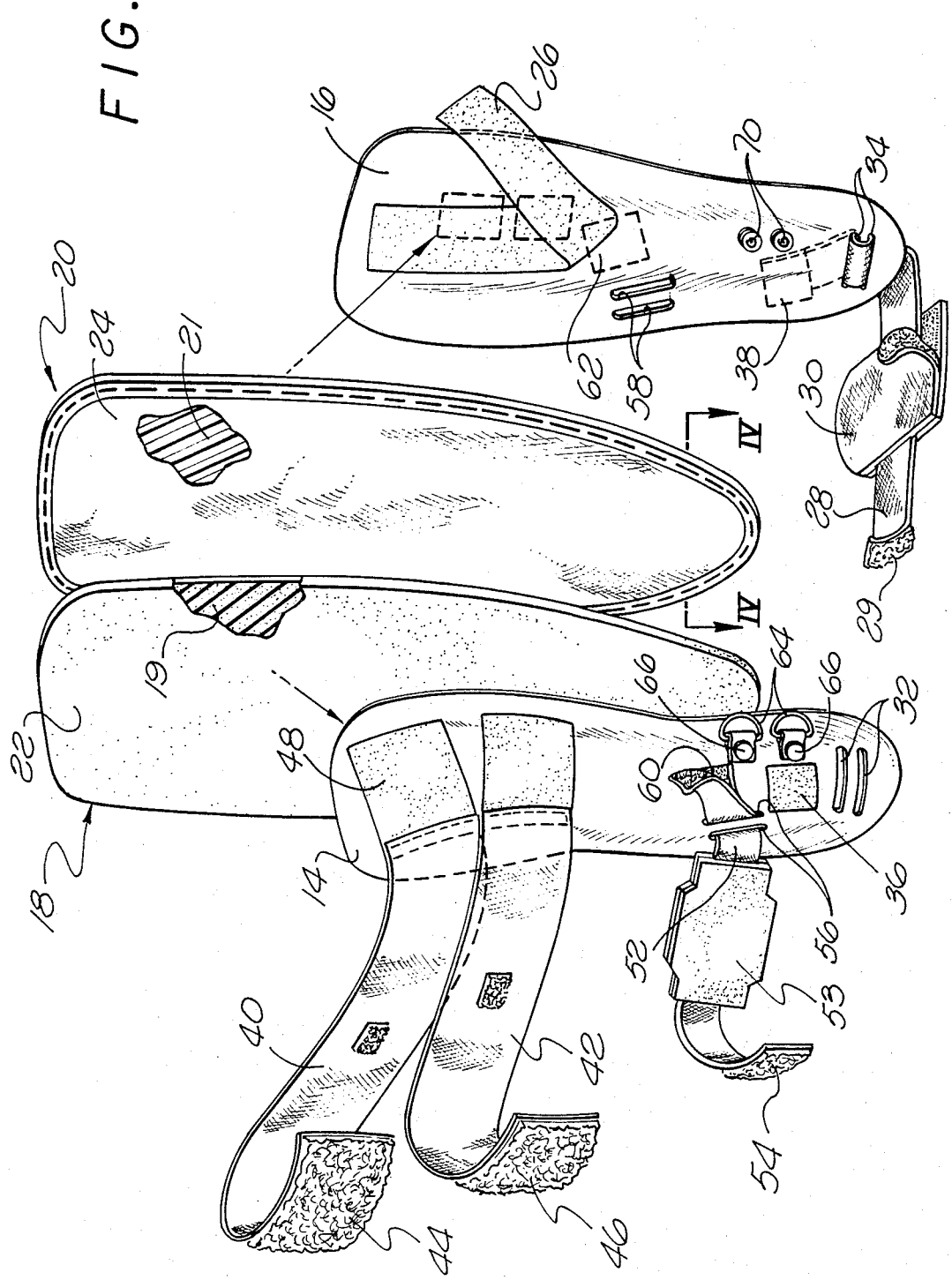

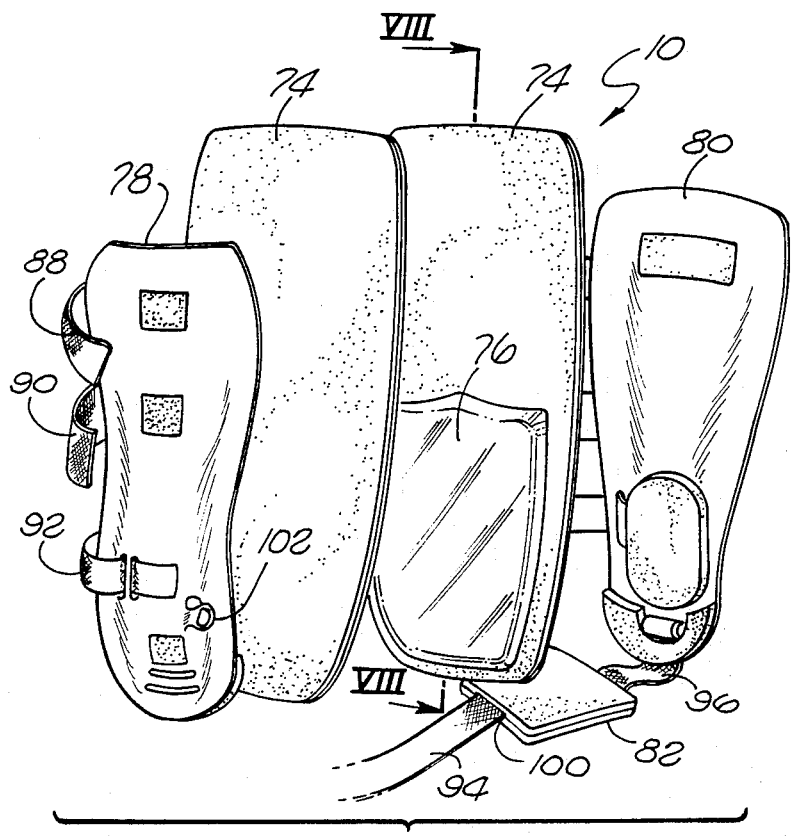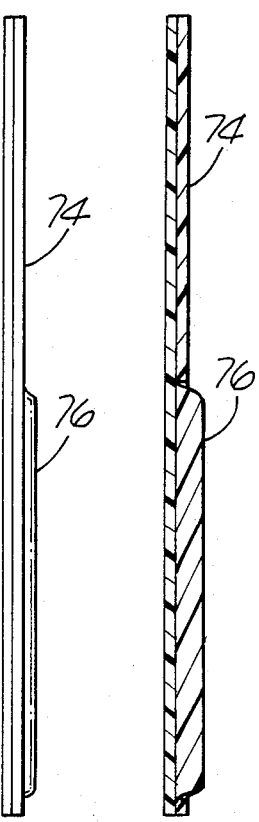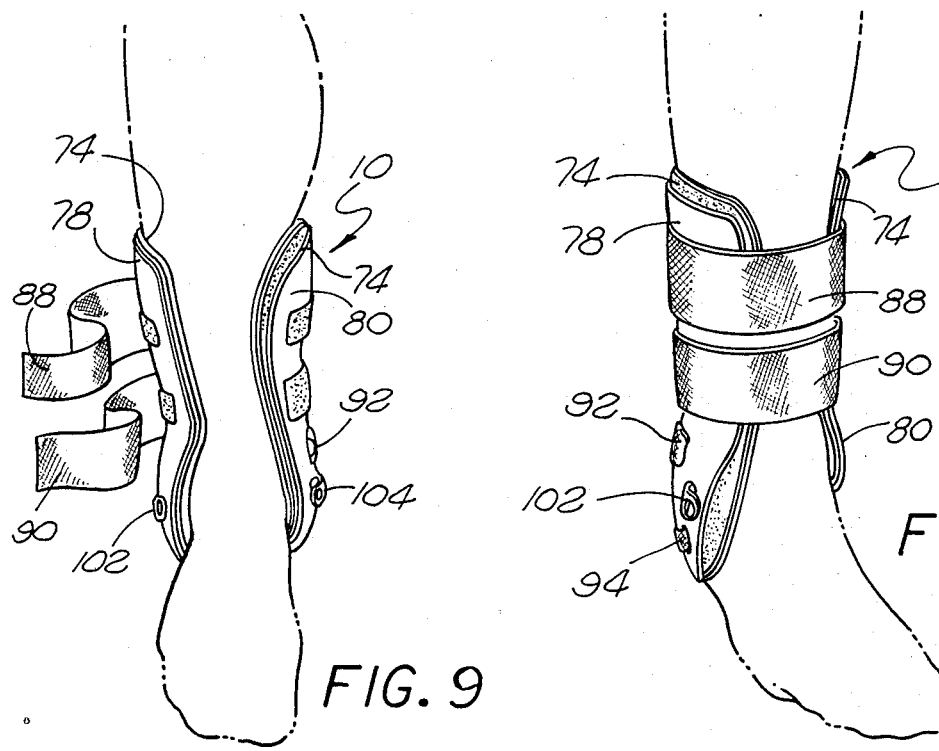
FIG. 6
FIG. 7  FIG. 8
FIG. 9
FIG. 10

ORTHOPEDIC DEVICE HAVING GEL PAD WITH PHASE CHANGE MATERIAL

CROSS-REFERENCE TO RELATED APPLICATIONS

The subject matter of this application is related to the subject matter of my co-pending U.S. patent application, Ser. No. 07/055,711, filed May 29, 1987, entitled "Ankle Brace," and assigned to Royce Medical Company, the assignee of the instant application, and is related to the subject matter of my co-pending U.S. patent application, Ser. No. 07/168,681, filed Mar. 16, 1988, entitled "Orthopaedic Gel Pad Method And Apparatus," also assigned to Royce Medical Company, the assignee of the instant application.

BACKGROUND OF THE INVENTION

The present invention relates generally to orthopedic devices and, more particularly, to an orthopedic device having at least one gel pad including at least one phase change material.

In the past, a variety of different orthopedic devices have been used to treat injured ankles, legs, knees, forearms, elbows, and other body limbs and parts by immobilizing or restricting the movement of the injured joint, limb or body part. For example, my co-pending U.S. patent application, Ser. No. 07/055,711, filed May 29, 1987, describes an orthopedic ankle brace using splint members and inner liners including gel pads for engaging and supporting an injured joint or limb. Another ankle brace using an air-inflatable liner is disclosed in U.S. Pat. No. 4,280,489, issued to Johnson, Jr. on Jul. 28, 1981. Still another inflatable ankle brace using air-inflatable liners or air bags is described in U.S. Pat. No. 4,628,945, issued to Johnson, Jr. on Dec. 16, 1986. The use of foam rubber pads or liners in a lower leg brace is disclosed in U.S. Pat. No. 4,572,169, issued to Mauldin, et al. on Feb. 25, 1986.

The gel pads used in my orthopedic ankle brace referred to above provide important advantages over the above-described braces using air-inflatable liners or foam rubber pads because, in addition to other important advantages, the gel pads may be used for hot and cold temperature therapy. Increased therapeutic effect can be achieved by selectively heating or cooling the gel pads before placing the pads in my orthopedic ankle brace. My co-pending U.S. patent application, Ser. No. 07/168,681, filed Mar. 16, 1988, describes a method of forming gel-filled cushion pads that may be heated or cooled for therapeutic purposes.

An example of a device using a gel-filled pack for cold therapy is described in U.S. Pat. No. 4,243,041, issued to Paul on Jan. 6, 1981. This patent describes a cold therapy pack used for the relief of pain, swelling, or other discomfort of patients having cosmetic surgery in the facial area. The cold therapy pack is a goggle-shaped plastic pack filled with a hydrophilic gel having the property of maintaining its pliability in a frozen state.

Therapeutic wraps containing refrigerant gels or coolants that may be wrapped around an injured limb such as an ankle, after the gels or coolants are cooled to a desired temperature, are described in U.S. Pat. Nos. 4,092,982, issued to Salem on Jun. 6, 1978, and 4,055,188, issued to Pelton on Oct. 25, 1977. A therapeutic elastic bandage containing bags filled with an antifreeze solution of propylene glycol in distilled water which may be cooled and used to cover an injured joint is shown in U.S. Pat. No. 3,900,035, issued to Welch, et al. on Aug. 19, 1975. Hot or cold compresses or wraps containing gels which may be wrapped, fit around or applied to a body part are disclosed in U.S. Pat. Nos. 3,885,403, issued to Spencer on May 27, 1975, and 3,780,537, issued to Spencer on Dec. 25, 1973, and British Patent No. 1,600,505, issued to Neave and dated Oct. 14, 1981. A hot or cold pack containing an absorbent pad, filled with a heated, cooled or frozen fluid such as water, which may be applied to a body part, is disclosed in U.S. Pat. No. 3,889,684, issued to Lebold on Jun. 17, 1975. A cold pack compression bandage containing a refrigerant gel which may be wrapped around a portion of a body is shown in European patent application No. 82302417.9 of Gordon, et al., dated Jan. 5, 1983.

Other cold pressure bandages or wraps using a refrigerant which may be fit around a body part are described in U.S. Pat. Nos. 3,717,145, issued to Berndt, et al. on Feb. 20, 1973, and 3,628,537, issued to Berndt, et al. on Dec. 21, 1971. A compression bandage impregnated with a hydrous gel for cooling and compressing an injured body part is described in U.S. Pat. No. 4,377,160, issued to Romaine on Mar. 22, 1983.

U.S. Pat. No. 4,756,311, issued to Francis, Jr. on Jul. 12, 1988, discloses a gel pack comprising an envelope fabricated from a laminate composed of film layers of dissimilar materials containing a gel composition including water, and a process of microwave heating the gel pack.

A gel pad useful in the prevention and treatment of decubitus ulcers (pressure sores) is fabricated by putting a thin-film envelope around a gel made by cross-linking high molecular weight polyvinyl alcohol, using a cross-linking agent, such as formaldehyde, in the presence of an acid catalyst such as hydrochloric acid, and by incorporating at least one internal plasticizer such as propylene glycol in the gel, is described in U.S. Pat. No. 3,858,379, issued to Graves, et al. on Jan. 7, 1975. Another gel cushion useful for protecting the body of a human or animal against localized pressures is manufactured by placing a sheet material around a gel comprising the reaction product of an organosiloxane and a hydrogenosiloxane, which is preferably a copolymer of a particular combination of siloxanes combined with an additive such as dimethylpolysiloxane, is disclosed in U.S. Pat. No. 3,663,973, issued to Spence on May 23, 1972.

Phase change materials may be used to improve the temperature storage capacity of different materials. U.S. Pat. No. 4,711,813, issued to Salyer on Dec. 8, 1987, discloses a polyethylene composition formed from cross-linked polyethylene having a straight chain (crystalline) alkyl hydrocarbon incorporated therein as a phase change material which may be manufactured as pellets or in sheet form. The polyethylene composition is for incorporation into concrete or other building materials and is used for wall or floor coverings, fire retardants, or runway, roadway or bridge de-icing, etc. U.S. Pat. No. 4,617,332, issued to Salyer, et al. on Oct. 14, 1986, describes a phase change composition comprising a cementitious matrix material selected from the group consisting of hydraulic cement, gypsum, lime and plaster of paris, and a plurality of pellets or granules containing a crystalline straight chain alkyl hydrocarbon or a mixture of crystalline, straight chain, alkyl hydrocarbons with the hydrocarbons having at least 14 carbon atoms and a heat of fusion greater than 30 cal/gm.

Encapsulated phase change materials in pellets for incorporation into concrete or other building materials are described in U.S. Pat. No. 4,504,402, issued to Chen, et al. on Mar. 12, 1985. The pellet-shaped product of this patent is formed of an outer seamless shell member which defines a cavity that permanently encases a phase change composition. The encapsulated phase change compositions described in the patent may be glauber salt eutectic mixture, sodium hydroxide, polyethylene, sodium sulfate decahydrate, sodium thiosulfate pentahydrate, calcium chloride hexahydrate, magnesium nitrate hexahydrate, the eutectic of magnesium nitrate hexahydrate and ammonium nitrate, potassium fluoride tetrahydrate, sodium acetate trihydrate, stearic acid, the eutectic of naphthalene and benzoic acid and paraffinic hydrocarbons. Shell materials described in the patent are copolymer latex of butadieneacrylonitrile, copolymer of vinylidene chloride-acrylic, resinous latexes, rubber latexes, epoxy polymers, polyurethane polymers, acrylic polymers, cellulose acetate and polyamides. Encapsulated phase change material particles are disclosed in U.S. Pat. No. 4,708,812, issued to Hatfield on Nov. 24, 1987. This patent describes encapsulated phase change material particles made by encapsulating with a continuous elastomeric, condensation polymeric shell phase change material particles selected from the group consisting of a crystalline polymer, naphthalene, salt hydrate and a crystalline paraffin.

Phase change materials that may be incorporated into building materials and used for other purposes are described in an article entitled "Advanced Phase-Change Materials for Passive Solar Storage Applications," by I. O. Salyer, et al., Society of Automotive Engineers, Inc., 1985, p. 3.699. The phase change materials discussed in this article are C-15 to C-24 crystalline alkyl hydrocarbons, tetrabutyl ammonium fluoride (and homologous) semiclathrates, acrylate and methacrylate polymers having C-16 to C-18 alkyl side chains, and polyethylene glycols having molecular weights between 600 and 3500. The phase change materials may be used for cement, concrete, plaster, plasterboard, floor tiles, foam insulation, textiles, paints, fire retardants, deicing of bridge decks and airport runways, keeping drinks at desired temperatures, etc. Another composition containing phase change material that may be used in the manufacture of building materials is described in U.S. Pat. No. 4,587,279, issued to Salyer, et al. on May 6, 1986. This patent describes a cementitious composition comprising an inorganic cementitious building material and an end-capped polyethylene glycol dispersed therein as a phase change material, the end-capped polyethylene glycol having a molecular weight greater than about 400 and a heat of fusion greater than about 30 cal/gm. The end-capped polyethylene glycol is selected from the group consisting of alkoxy-capped polyethylene glycol, urethane-capped polyethylene glycol, and ester-capped polyethylene glycol.

Polyethylene glycol has been used as a phase change material in thermal energy storage clothing. The polyethylene glycol phase change material is attached to the fibers of the clothing and absorbs large amounts of heat when it melts or softens, and releases large amounts of heat when it solidifies.

SUMMARY OF THE INVENTION

The therapeutic value of gel pads used in orthopedic devices would be improved by adding a phase change material to the gel material contained in the pads, thereby improving the thermal energy storage capacity of the pads, allowing the pads to absorb and release much more energy during hot and cold temperature therapy. Moreover, the therapeutic value of a gel pad would be improved if two different phase change materials were added to the gel material, one of which could be used for cold temperature therapy while the other could be used for hot temperature therapy.

None of the orthopedic devices or references discussed above uses, discloses or suggests using gel pads including phase change material to improve the thermal energy storage capacity of the pads so that the pads will absorb and release more energy than pads only containing gel material. Accordingly, there is a need for an orthopedic device having at least one gel pad including at least one phase change material.

It is an object of this invention to provide an orthopedic device having at least one gel pad including at least one phase change material for improving the thermal energy storage capacity of the gel pad.

It is another object of this invention to provide a gel pad including at least one phase change material which is adaptable for use in a variety of different orthopedic devices that may be removed from an orthopedic device and heated or cooled and then placed back in the device for hot or cold temperature therapy.

It is still another object of this invention to provide a gel pad including two different phase change materials, one of the phase change materials is capable of being used for cold temperature therapy while the other is capable of being used for hot temperature therapy.

It is still another object of this invention to provide a gel pad including a phase change material having a freezing temperature in the range of about 20 degrees Fahrenheit to about 35 degrees Fahrenheit.

It is still another object of this invention to provide a gel pad including a phase change material having a freezing temperature in the range of about 45 degrees Fahrenheit to about 55 degrees Fahrenheit.

It is still another object of this invention to provide a gel pad including a phase change material having a melting temperature in the range of about 95 degrees Fahrenheit to about 125 degrees Fahrenheit.

It is still another object of this invention to provide a gel pad including a phase change material having a heat of fusion in the range of about 30 cal/gm to about 65 cal/gm.

It is still another object of this invention to provide a gel pad including a phase change material having a heat of fusion in the range of about 20 cal/gm. to about 35 cal/gm.

It is still another object of this invention to provide a gel pad including a phase change material having a ratio of phase change material to gel material by weight of about 50 percent.

These and other objects and advantages are attained by an orthopedic device for treatment of injured joints or limbs, having at least one gel pad including at least one phase change material for improving the thermal energy storage capacity of the gel pad. The phase change material included in the gel material inside the gel pad may be encapsulated, formed in pellets, soluble, insoluble, or in any desired form. The gel pad may be removed from the orthopedic device, heated or cooled, and then reused with the device for hot or cold therapy of injured joints or limbs, taking advantage of the increased thermal energy storage capacity of the phase change material. Two different phase change materials may be included in the gel pad, one of which may be used for cold temperature therapy while the other is used for hot temperature therapy. The gel pad may include encapsulated water as phase change material. Even when the gel pad is cooled to a temperature of 20 degrees Fahrenheit to 30 degrees Fahrenheit, the gel material does not solidify. This is important because the flexible gel pad with phase change material will conform to the shape of the injured limb or joint evenly supporting or cushioning the limb or joint, resulting in a uniform hot or cold temperature distribution over the injured body parts.

The combination of gel with liquid/solid phase change material has certain special advantages. Thus, for example, when a flexible bag of cubes or small pieces of ice is used for cold therapy, the sharp corners of the ice may engage the tender, injured part of the body and cause discomfort to the user. However, when the phase change material is included within the gel, the flexible and conforming nature of the gel, together with the excellent heat transfer properties and high heat capacity of the gel, produce a combination which is comfortable for the user, as well as having greatly increased heat transfer capacity as a result of the combined latent and sensible heat capacities of the resultant combination.

A sheet of encapsulated phase change material may be used inside the gel pad. The phase change material is encapsulated in bubbles or capsules formed as part of the sheet. Since the phase change material is encapsulated in a sheet, it is not free to move around inside the gel pad. This provides advantages over gel pads containing encapsulated phase change materials that move inside the pads, or phase change materials in the form of pellets that are free to move, because such moving phase change materials may produce non-uniform temperature for hot or cold therapy, or may press up against the outer cover or sheet of the gel pad producing a lumpy or unpleasant feeling.

The various features of the present invention will be best understood together with further objects and advantages by reference to the following description of the preferred embodiments taken in conjunction with the accompanying drawings.

BRIEF DESCRIPTION OF THE DRAWINGS

FIG. 1 is a perspective view of an ankle brace orthopedic device having a gel pad including phase change material, illustrating certain aspects of the present invention, fitted in association with a shoe;

FIG. 2 is an exploded perspective view of the various parts of the orthopedic device of FIG. 1 showing the gel pad including phase change material;

FIG. 3 is a cross-sectional view of the orthopedic device taken in the direction of arrows III—III of FIG. 1;

FIG. 4 is an enlarged cross-sectional view of the gel pad taken in the direction of arrows IV—IV of FIG. 2 showing phase change material included in gel material inside the gel pad;

FIG. 5 is an enlarged cross-sectional view of a typical encapsulated phase change material;

FIG. 6 is an exploded perspective view of a walking brace orthopedic device having gel pads including phase change material illustrating certain aspects of the present invention;

FIG. 7 is a side elevational view of one of the gel pads of FIG. 6;

FIG. 8 is a cross-sectional view of one of the gel pads taken in the direction of arrows VIII—VIII of FIG. 6;

FIG. 9 is a perspective view illustrating how the gel pads are used as part of the walking brace orthopedic device to support an injured ankle;

FIG. 10 is a perspective view illustrating how straps on the walking brace orthopedic device are used to provide a firm grip around the lower leg with the gel pads resiliently supporting the ankle;

FIG. 15 is an enlarged cross-sectional view of the gel pad taken similar to FIG. 4 showing two different phase change materials included in gel material inside the gel pad; and FIG. 16 is an enlarged cross-sectional view of the gel pad taken similar to FIG. 4 showing a sheet of encapsulated phase change material inside the gel pad.

DESCRIPTION OF THE PREFERRED EMBODIMENTS

Figure 11:
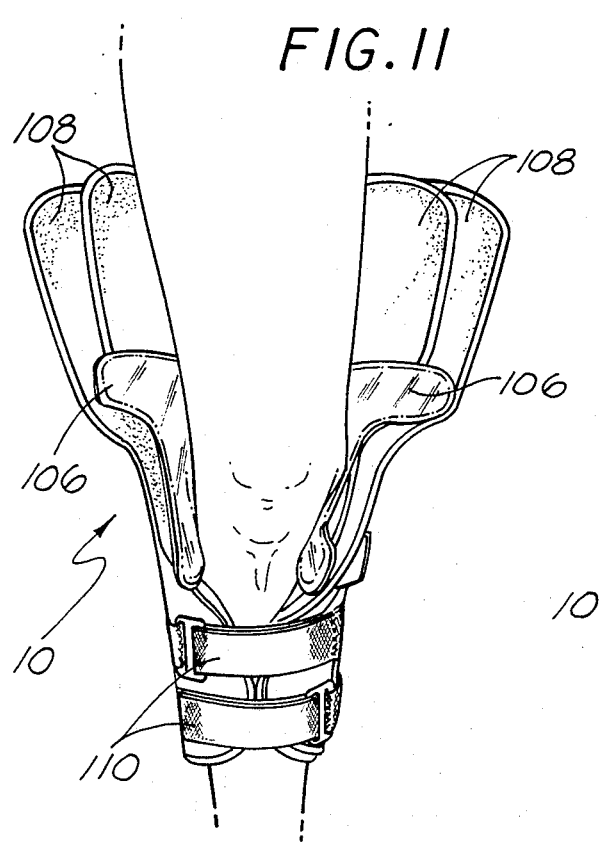
FIG. 11 is a front elevational view of a knee brace orthopedic device having gel pads including phase change material, illustrating certain aspects of the present invention, showing upper portions of pad members unfolded to reveal the gel pads.

The following specification taken in conjunction with the drawings sets forth the preferred embodiments of the present invention in such a manner that any person skilled in the art can use the invention. The embodiments of the invention disclosed herein are the best modes contemplated by the inventor for carrying out his invention in a commercial environment although it should be understood that various modifications can be accomplished within the parameters of the present invention.

Referring to FIGS. 1 through 4, an ankle brace embodiment of the orthopedic device 10 of the present invention is shown fitted within the shoe 12 of an injured person. Referring specifically to FIGS. 1 and 2, the ankle brace orthopedic device 10 is formed as a stirrup including a pair of side support members 14 and 16 made of rigid plastic which is typically vacuum formed to conform to the shape of the lower leg. Positioned within the side support members are resilient pad members 18 and 20 which are preferably formed of a dense material. Specifically, the resilient pad member 18 is shown to be a dense foam material 19 and the resilient pad member 20 is shown to be a gel pad 20 having combined gel material 21 and phase change material 25 contained therein. Of course, both pads would normally be formed of the same material, but it is to be appreciated that different materials as well as combinations of gel and foam may be used to form the pads. However, the orthopedic device 10 has at least one gel pad 20. In any event, the resilient pads 18 and 20 provide for a cushion effect against the lower extremity of the lower leg and foot, fitting or conforming to the shape of the leg or foot, while at the same time firmly supporting the ankle.

Preferably, the gel material 21 included with the phase change material 25 in the pad 20 is of the type sold under the trademark (ELASTO GEL) by Southwest Technologies, Inc. of Kansas City, Mo., which gel material includes a glycerine and polyacrylamide based material and water, and has thermal properties to allow the gel to be either pre-heated or cooled, so as to provide for added therapeutic effect. Attention is also directed to U.S. Pat. No. 4,671,267, issued to Stout on Aug. 1, 1986, which discloses the method of making the gel, the disclosure of which is hereby incorporated by reference. The dense gel material 21 provides for desired flexibility and comfort. In addition, the dense foam and gel material 19 and 21 are covered with materials 22 and 24, respectively, which materials may be a fabric, film or sheet such as urethane, vinyl, resin, plastic, or the like, to provide for additional comfort.

The resilient pads 18 and 20 may be attached to the inside of the side supports 14 and 16 using known means such as double sides adhesive 26 shown on side support 16 or some other attachment means such as strips attached to the side supports and the pads. Such strips may be made of material marketed under the trademark (VELCRO) which causes the strips to cling to each other when pressed together. (VELCRO) material includes cooperating male and female portions. The male portion includes a plurality of miniature hooks covering the outwardly facing surface thereof that detachably engage the mating surfaces of the female portion. The female portion comprises a fine mesh material which includes a plurality of loops into which the male hooks extend for engagement therewith. The male and female portions may be pulled apart after being pressed together. It is to be appreciated that side support 14 has a similar attachment means on its inside surface.

Interconnecting the two side supports 14 and 16 is a bottom strap 28 which includes a pad member 30. The bottom strap 28 may include a surface 29 of velcro material and with the bottom strap being adjustable through the use of double openings 32 and 34 in the side supports. The ends of the bottom strap 28 may be fixed in position with the use of additional (VELCRO) material 36 and 38 located on the outsides of the side support members 14 and 16. Specifically, the adjustment is accomplished by positioning the ends of the strap 28 to extend from the outside of each side support member through a first one of the openings 32 and 34 and then back out through the other one of the openings 32 and 34 and then attached by the velcro material 36. The proper distance therefore may be easily adjusted between the side support members 14 and 16 at the lowermost position.

The side supports may be also tightly attached around the leg just below the calf area using the two strap members 40 and 42. These strap members also include (VELCRO) portions on their outside surfaces, as shown by (VELCRO) material 44 and 46, and with (VELCRO) material 48 and 50 at the end portions of the straps. The (VELCRO) 48 and 50 is attached to the side supports 14 and 16. As shown in FIG. 1, these straps 40 and 42 may be tightly drawn around the leg and secured using the (VELCRO) material so that the upper portion of the ankle brace is tightly supported around the leg below or around the calf area.

The orthopedic device 10 includes a counter strap 52 located above the heel, similar to the bottom strap 28. Specifically, the counter strap 52 includes a pad 53 and an inner surface of (VELCRO) material 54 and with the strap passing through double openings 56 in the side support 14 and double openings 58 in the side support 16. A further piece of (VELCRO) material 60 is attached to side support 14 and a piece of (VELCRO) material 62 is attached to side support 16. In this way the counter strap 52 may be adjusted in a similar manner to the bottom strap 28 to hold the back portion of the side support means 14 and 16 from twisting or flexing outward at the lower end of the ankle brace to compress the distal $\frac{1}{3}$ to $\frac{1}{2}$ of the brace.

In order to insure that the front portion of the side supports 14 and 16 do not twist or flex outward, the orthopedic device 10 includes fastening means provided on the side supports which cooperate with laces 72 of the shoe 12 to compress the distal $\frac{1}{3}$ to $\frac{1}{2}$ of the brace. Specifically as shown in the drawings, this fastening means may be D-rings which are riveted to the side supports. Specifically, side support 14 may include a pair of D-rings 64 attached by rivets 66. Side support 16 may include a similar pair of D-rings 68 attached by rivets 70.

Limb injuries are accompanied by swelling of the injured area. Applying cold materials to the injury can minimize the swelling, thus reducing the recovery time, if done immediately after sustaining the injury. After swelling has ceased, applying heat to the injury can stimulate blood flow and speed the healing process.

The gel pad 20 with gel material 21 and phase change material 25 may be used to provide hot or cold therapy by heating or cooling the gel material 21 using appropriate techniques. For example, cooling would normally be provided by placing the pads in a freezer. Heating would occur by using a microwave oven or placing the pad 20 into boiling water. The pads would then be attached to the inside of the side supports 14 and 16 using the fastening means.

The thermal energy storage capacity of the gel pad 20 or gel material 21 is improved by adding phase change material 25 (see FIG. 4) to the gel material 21 so that the pad 20 absorbs and releases more energy than pads only containing gel material. Phase change materials have a higher capacity to store energy, and they absorb and release a large quantity of energy over a very narrow temperature range. Phase change material may be selected to provide more or less heat at exact temperatures. This will aid the healing process by exposing sensitive tissues to hot or cold temperatures promoting healing and/or control of edema or swelling. In addition, by using phase change material having a phase change temperature in the optimum temperature control range, the length of time at other temperatures is minimized, and the period of time with optimum temperature is increased. A phase change material utilizes its latent heat of fusion for thermal storage. The latent heat of fusion of the phase change material is substantially greater than the sensible heat capacity of the material. Upon melting and freezing, per unit weight, a phase change material absorbs and releases substantially more energy than a sensible heat storage material which is heated or cooled to the same temperature range. Phase change materials also store and release sensible energy as well. Thus, the latent storage in phase change materials is always augmented to a significant extent by their sensible storage capacity. Latent energy storage in a material results from a change of state of the material, i.e., solid to liquid, etc., whereas sensible energy storage results from a change in temperature of the material.

The phase change material 25 included in the gel material 21 of gel pad 20 may be any organic phase change material such as paraffin waxes, which, for the most part, consist of a mixture of straight chain paraffins or N-alkanes, or stable organic polymers like polyethylene glycols. Salt hydrates and fused salts (inorganic materials) may also be used for the phase change material 25 such as sodium sulfate decahydrate/salt mixtures. Gelled phase change materials can also be used for phase change material 25 such as gelled strong salt solutions, or gelled $CaCl_2.6H_2O/CaBr_2.6H_2O$. Also a class of N-acyl amino acid derivatives have the property of gelatinizing various fats and oils and may provide suitable phase change materials 25. The phase change material 25 may be soluble or insoluble.

Some commercially available phase change materials which may be used for phase change material 25 are listed below.

| Phase Change Material | Type | Melting Point (Degrees Centigrade) |
| --- | --- | --- |
| $MgCl_2.6H_2O$ | Quasi-congruent | 117 |
| $Mg(NO_3).6H_2O$ | Congruent | 89 |
| $Na_4P_2O_7.10H_2O$ | Incongruent | 70 |
| $NaOAc.3H_2O$ | Incongruent | 58 |
| $MGCl_2.6H_2O/$ $Mg(NO_3)_2.6H_2O$ | Eutectic | 58 |
| Paraffin wax | Congruent | 50 |
| $Na_2S_2O_3.5H_2O$ | Semicongruent | 48 |
| Neopentyl glycol | Congruent | 43 |
| $CaBr_2.6H_2O$ | Congruent | 34 |
| $Na_2SO_4.10H_2O$ | Incongruent | 32 |
| $CaCl_2.6H_2O$ | Semicongruent | 28 |
| Polyethylene glycol | Congruent | 23 |
| $Na_2SO_4.10H_2O/$ NaCl | Incongruent | 18 |
| $CaBr_2.6H_2O/$ $CaCl_2.6H_2O$ | Isomorphous | 15 |
| $Na_2SO_4.10H_2O/$ KCl/$NH_4Cl$ | Incongruent | 8 |

Phase change material 25 used in the gel material 21 of gel pad 20 may be contained in a material composition such as the polyethylene composition formed from cross-linked polyethlene having a straight chain crystalline alkyl hydrocarbon therein as a phase change material disclosed in U.S. Pat. No. 4,711,813, issued to Salyer on Dec. 8, 1987, the disclosure of which is hereby incorporated by reference. The polyethylene composition containing phase change material described in the patent may be fabricated as pellets, which is a preferred form for the phase change material 25 used for the gel pad 20 of the orthopedic device 10 of the present invention.

The phase change material 25 or material composition containing phase change material 25 may also be encapsulated inside a thin film 26 (see FIG. 5) of vinyl, urethane, copolymer latex of butadiene-acrylonitrile, copolymer of vinylidene chloride-acrylic, resinous latex, rubber latexes, epoxy polymers, polyurethane polymers, acrylic polymers, cellulose acetate, polyamides, any resin, or the like. However, any suitable film 26 may be used and any phase change material 25 or composition containing the phase change material 25 may be encapsulated in any convenient manner using any existing technique for incorporation into the gel material 21 of the orthopedic device 10 of the present invention.

Other phase change materials 25 which may be used in the gel pad 20 of the orthopedic device 10 of the present invention are crystalline alkyl hydrocarbons having 15 to 24 carbon atoms, tetrabutyl ammonium fluoride (and homologous) semiclathrates, acrylate and methacrylate polymers having alkyl side chains with 16 to 18 carbon atoms, and polyethylene glycols having molecular weights between 600 and 3500.

The heated or cooled gel pad 20 with phase change material 25 is placed back into the orthopedic device 10 for hot or cold therapy. Even when the gel pad 20 is cooled to a temperature of 20 degrees Fahrenheit to 30 degrees Fahrenheit, the gel material 21 does not solidify. This is important because the flexible gel pad 20 with phase change material 25 will conform to the shape of the injured limb or joint evenly supporting or cushioning the limb or joint, resulting in a uniform hot or cold temperature distribution over the injured body part.

Preferably the phase change material 25 has a freezing temperature in the range of about 45 degrees Fahrenheit to about 55 degrees Fahrenheit. Temperatures below 45 degrees Fahrenheit cause undue discomfort to a patient while temperatures above 55 degrees Fahrenheit are not beneficial for minimizing swelling. However, phase change material 25 with a freezing temperature in the range of about 20 degrees Fahrenheit to about 35 degrees Fahrenheit may be desirable where low temperature therapy is desirable.

By way of example but not of limitation, water may be used as the phase change material 25 for use in cold therapy because its freezing point, 32 degrees Fahrenheit, falls within the desirable lower range discussed above for low temperature therapy. One gram of ice requires 82 calories of heat for its phase change to water, at 0 degrees Centigrade or 32 degrees Fahrenheit, and absorbs 1 calorie for every degree Centigrade of increased temperature involving sensible heat transfer without phase change.

The combination of phase change material 25 with gel material 21 is particularly advantageous in view of the relatively high heat capacity of the gel material 21. Thus using a gel material 21 which stays in the same state over a broad temperature range, e.g., when cooling an injured body part to about 40 degrees Fahrenheit which will not cause the gel material 21 to solidify, allows a phase change material 25 to be selected having a freezing point of about 40 degrees Fahrenheit and the gel pad 20 to be filled with such phase change material 25 either encapsulated or in pellet form. The gel pad 20 may then be cooled to about 35 degrees Fahrenheit so that the phase change material 25 is in the solid state, and is then applied to the injured body part. The pad 20 initially cools the injured body part by absorbing sensible heat, until 40 degrees Fahrenheit is reached, and then subjects the injured body part to substantial cooling as the phase change material 25 melts or becomes liquid. The phase change material 25 will continue to absorb substantial heat as it melts over a period of time since all of the phase change material 25 will not melt instantly at the same time. Thereafter, further sensible heat transfer occurs as the liquid phase change material 25 and the gel material 21 heat up. Throughout this process the high thermal capacity of the gel material 21 and its flexibility serve to buffer and facilitate the heat transfer between the gel pad 20 and the injured body part.

When it is desirable to use hot temperature therapy to heat an injured body part, for example, to a temperature of about 105 degrees Fahrenheit, a phase change material 25 can be chosen, for example, from straight chain (crystalline) alkyl hydrocarbons in pellet form having from 20 to 23 carbon atoms which have a melting point in the range of about 95 degrees Fahrenheit to about 122 degrees Fahrenheit. After the proper alkyl hydrocarbon phase change material 25 is chosen that has the desirable 105 degree Fahrenheit melting point, the gel pad 20 and gel material 21 with phase change material 25 is heated past 105 degrees Fahrenheit to about 115 degrees Fahrenheit so that the phase change material 25 melts, and the gel pad 20 is then applied to the injured body part. The pad 20 initially heats the injured body part by giving off sensible heat, until 105 degrees Fahrenheit is reached as the temperature of the pad 20 decreases, and then subjects the injured body part to substantial heating as the phase change material 25 hardens or becomes a solid from its melted state. The phase change material 25 will continue to give off substantial heat as it continues to solidify over a period of time since all of the phase change material 25 will not solidify instantly at the same time.

When phase change material 25 with low freezing temperatures (e.g., 25 degrees Fahrenheit) and high melting temperatures (e.g., 120 degrees Fahrenheit) are used for cold and hot temperature therapy, respectively, a user may wear clothing, padding, etc. between a gel pad 20 used for therapy and an injured body part in order to avoid discomfort due to the extremely cold or hot pad 20. Of course, the gel pad 20 may be applied directly to the injured body part, or without clothing or padding between the pad 20 and injured part, if desired.

A phase change material 25 is preferred with a melting temperature in the range of about 95 degrees Fahrenheit to about 125 degrees Fahrenheit, and the preferred melting temperature is about 105 degrees Fahrenheit. Any phase change materials 25 may be used such as the straight chain (crystalline) alkyl hydrocarbons in pellet form mentioned above to select any desirable melting temperature for hot temperature therapy.

The phase change materials described above are preferred materials for the phase change material 25 used for the gel pad 20. However, any phase change material 25 that improves the thermal energy storage capacity of the gel material 21 in the gel pad 20 may be used. Preferably, the phase change material 25 has a heat of fusion in the range of about 30 cal/gm to about 65 cal/gm which represents phase change materials such as paraffin waxes and alkyl hydrocarbons, and in the range of about 20 cal/gm to about 35 cal/gm which represents other phase change materials such as polyethylene glycols. In addition, the ratio of phase change material 25 to gel material 21 by weight is preferably about 50 percent. However, more or less phase change material 25 may be used as desired.

The gel pad 20 including the phase change material 25 may be removed from the orthopedic device 10 and cooled or heated and then placed back into the device 10 as desired. Since the gel pad 20 including phase change material 25 may be removed, it may be used in different orthopedic devices 10, and the shape or size of the gel pad 20 may be varied as desired to facilitate use in different orthopedic devices 10.

A walking brace embodiment of the orthopedic device 10 of the present invention is shown in FIGS. 6 through 10. The orthopedic device 10 has two resilient pad members 74 with a gel pad 76 attached to each of the members 74. The gel pads 76 conform to the shape of an injured ankle offering cushioning effect and firm and resilient support. Each of the gel pads 76 contains gel material 21 with phase change material 25 incorporated therein. As such, the pad members 74 may be removed and the gel pads 76 can be heated or cooled for hot or cold therapy purposes taking advantage of the increased thermal energy storage capacity of the phase change material 25.

FIG. 6 is an exploded perspective view of the walking brace orthopedic device 10 illustrating the manner in which the pad members 74 are used in the orthopedic device 10. Each of the gel pads 76 are used to provide a resilient support against the ankle on each side of the leg. Pad members 74 may be attached to support walls 78 and 80 using velcro type material or other similar means. The two pad members 74 and the stiff support walls 78 and 80 each have matching (VELCRO) pads. The gel pad units and the support walls may also have oppositely paired (VELCRO) pads at their top and bottom so that the gel pads may not be mounted on the side walls upside down.

To further support the leg, a U-shaped stirrup member 100 is used. Stirrup member 100 includes a base plate or pad member 82 and straps 94 and 96. The base plate or pad member 100 extends underneath the heel of the user. The straps 94 and 96 are used for firmly attaching the base plate 100 to the side wall supports 78 and 80, respectively.

The side support walls 78 and 80 may better support the leg when a counter strap 92 is used just above the heel to further limit the side walls 78 and 80 from moving outward relative to the ankle. In addition, the bottom portion of the side walls 78 and 80 may be inserted in a shoe. With the bottom portion of the walking brace inserted in the shoe, the lace fastening loops 102 and 104 may be used to tightly secure the orthopedic device 10 on the foot in the ankle area. This is done by passing the shoe lace through the D-shaped loop members 102 and 104 and then bringing the shoe laces back to the front and tying them together.

FIG. 9 illustrates the manner in which the walking brace orthopedic device 10 is put on, with the pad members 74 and gel pads 76 providing a comfortable, cushioning, firm and resilient support against the ankle. As shown, the pad members 74 and gel pads 76 substantially conform to the shape of the leg, providing a uniform temperature distribution to the injured portions of the leg or ankle from the heated or cooled pads 76. Further, the side support walls 78 and 80 provide for a firm support against the leg. The straps 88 and 90 are used to firmly hold the walking brace around the leg. This is better shown in FIG. 10.

FIG. 10 illustrates the manner in which the walking brace orthopedic device 10 is secured. As shown, the upper part of the leg is firmly supported using the straps 88 and 90. The mid and lower portion of the leg is supported by strap 90 and counter strap 92. The lower portion of the leg is supported by the counter strap 92 and lace members 102, 104, and the U-shaped stirrup member 100.

Figure 12:
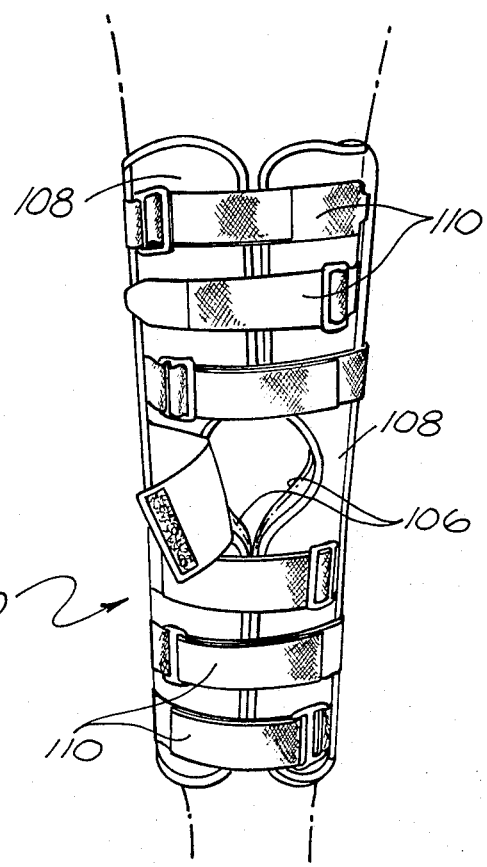
FIG. 12 is a front elevational view of the knee brace orthopedic device of FIG. 11 illustrating how straps provide a firm grip around the leg and knee with the gel pads helping to resiliently support the knee under the pad members.

A knee brace embodiment of the orthopedic device 10 of the present invention is shown in FIGS. 11 and 12. The orthopedic device 10 has gel pads 106 sized and shaped to fit around an injured knee as shown. Each of the gel pads 106 contains gel material 21 with phase change material 25 contained within the gel material 21. The gel pads 106 provide increased support and cushioning effect and are held around the knee by pad members 108 which are secured to a user's leg and around the knee by a plurality of straps 110 using (VELCRO) type fasteners. Upper portions of the pad members 108 are shown unfolded in FIG. 12 to reveal the gel pads 106. As discussed above, the gel pads 106 including phase change material 25 may be removed, heated or cooled and then used with the knee brace orthopedic device 10 to take advantage of the improved thermal energy storage capacity of the gel material 21 with phase change material 25 incorporated therein for hot or cold therapy.

Figure 13:
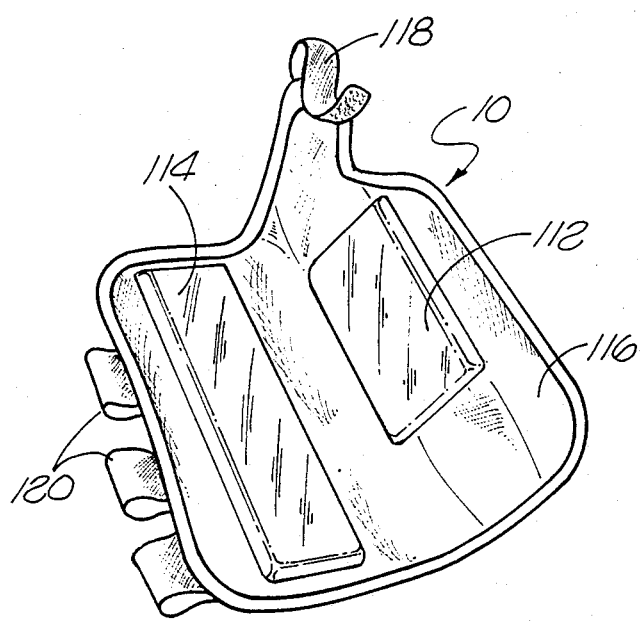
FIG. 13 is a perspective view of a wrist-forearm brace orthopedic device having gel pads including phase change material, illustrating certain aspects of the present invention.
Figure 14:
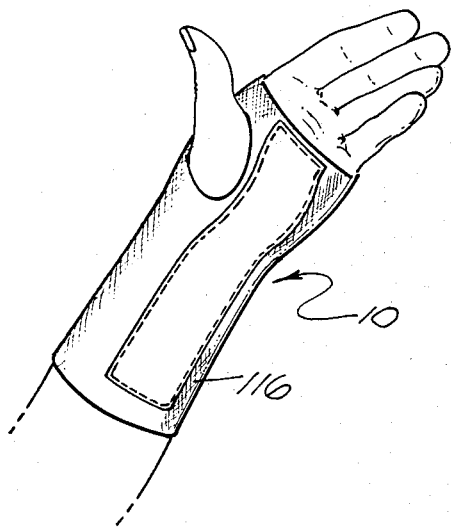
FIG. 14 is a perspective view of the wrist-forearm brace orthopedic device of FIG. 13 illustrating how the device supports a wearer's wrist and forearm.

FIGS. 13 and 14 show a wrist-forearm brace embodiment of the orthopedic device 10 of the present invention. The orthopedic device 10 has two gel pads 112 and 114 including phase change material 25 which fit inside a pad member 116 and provide increased support and cushioning effect for the wrist and forearm of the user. Straps 118 and 120 are used to secure the pad member 116 and gel pads 112 and 114 to the wrist and forearm of the user. As explained above, the gel pads 112 and 114 including phase change material 25 may be removed, heated or cooled, reinserted into pad member 116, and then strapped around a user's wrist and forearm for hot or cold therapy, taking advantage of the increased energy storage capacity of the phase change material.

The gel pads 20, 76, 106, 112 and 114 including phase change material 25 may be used with any type of orthopedic device 10. It is intended that the present invention not be limited to the orthopedic devices 10 shown in the drawings and described in the specification. For example, orthopedic devices 10 used for injured elbows, necks, or other body limbs or parts may be used with the gel pads including phase change material. Also, the size and shape of the gel pads may vary as desired in order to adapt the pads to any particular type of orthopedic device. The phase change material 25 may be soluble or insoluble and in any desirable form other than as pellets and does not have to be encapsulated. It may be in powder, wax, liquid, solid or other forms. Water may be used as a phase change material 25 for the present invention described herein. The phase change material 25 may be mixed with other materials or may be in composite form before being added to the gel material 21 or may be added directly to the gel material 21 without any other materials present. In other words, any type or form of phase change material 25 may be added to the gel material 21.

FIG. 15 shows another embodiment of the gel pad 20 of the present invention. The gel pad 20 contains gel material 21 with two different phase change materials 102 and 104 included in the gel material 21. The gel material 21 is covered, preferably, by a fabric, film or sheet 24 made out of urethane, vinyl, resin, plastic, tightly woven fabric, or the like. The phase change materials 102 and 104 may be any type of phase change materials such as those described above for phase change material 25 used for the gel pad 20 shown in FIG. 4. Preferably, the phase change materials 102 and 104 have different melting or freezing temperatures so that the gel pad 20 may be used for both hot and cold temperature therapy. For example, if phase change material 102 has a freezing temperature of about 40 degrees Fahrenheit and phase change material 104 has a melting temperature of about 105 degrees Fahrenheit, then phase change material 102 can be used for cold therapy while phase change material 104 may be used for hot therapy, as explained in the previous discussion. Thus, the gel pad 20 with two different phase change materials 102 and 104 is a multipurpose pad and may be used for both hot and cold temperature therapy.

It is important to note that the heat of fusion values of the phase change materials 102 and 104 may be chosen as desired for therapeutic reasons. Also, more than two phase change materials may be used to cover a broader range of hot or cold temperature therapy applications. For example, a third phase change material (not shown) may be chosen that has a freezing temperature of 25 degrees Fahrenheit which could be used for low temperature therapy.

Another embodiment of the gel pad 20 of the present invention is shown in FIG. 16. The gel pad 20 contains gel material 21 covered by upper and lower fabrics, films or sheets 106 and 108 made out of urethane, vinyl, resin, plastic, or the like. Sheets 106 and 108 may be one continuous sheet or formed separately and later joined together. Attached to sheet 108 are a plurality or sheet of bubbles or capsules 110 containing phase change materials 112 and 113 so that the phase change materials 112 and 113 are encapsulated in capsules 110 and not free to move or migrate around inside the gel pad 20. The capsules 110 may be made out of the same fabric, film or sheet material used for sheets 106 and 108 and may be formed separately and attached to sheet 108, or fabricated as an integral part of sheet 108. Since the phase change materials 112 and 113 do not move inside the gel pad 20, this pad design provides advantages over gel pads containing encapsulated phase change materials or phase change materials in pellet form that are free to move around inside the pad which may produce an uneven distribution of the phase change materials throughout the pad, or non-uniform temperature distribution for therapy. Also, phase change materials free to move within the pad may press up against the outer sheet of the pad producing a lumpy or unpleasant feeling, for example, when ice or hard pellets are used for phase change materials.

The same phase change material may be used for the phase change materials 112 and 113 in the capsules 110. However, different phase change materials may be used in the capsules 110 if desired, for example, a cold therapy phase change material 112 and a hot therapy phase change material 113 may be used. Water may be used as one or both of the phase change materials 112 and 113. In addition, water may be used for any of the phase change materials 25, 102 and 104 shown in FIGS. 4 and 15, respectively. Water is economical, may be reused numerous times and provides desirable thermal characteristics for cold temperature therapy.

The above description discloses the preferred embodiments of the present invention. However, persons of ordinary skill in the art are capable of numerous modifications once taught these principles. Thus, by way of example and not limitation, the gel material contained in the gel pad may be prepared as a composition containing phase change material as one of the components of the composition, or the phase change material may be placed in the gel material in sheet, rod or other form, or may be attached to or part of the sheet or envelope surrounding the gel material inside the gel pad. Accordingly, it will be understood by those skilled in the art that changes in form and details may be made to the above-described embodiments without departing from the spirit and scope of the invention.

We claim:

1. An orthopedic device for supporting an injured body member and providing temperature therapy to the member comprising:
   means for providing support to said injured body member;
   gel pad means adapted to be mounted between said supporting means and said injured body member for cooperating with said supporting means to provide resilient support and cushioning effect between said injured body member and said supporting means and for selectively providing temperature therapy to said injured body member, said gel paid means including gel material having at least one phase change material contained therein, said phase change material providing increased thermal storage capacity to said gel material, said gel pad means capable of being removed from between said supporting means and said injured body member so that the temperature of said gel pad means may be changed, and then placed between said injured body member and said supporting means in order to provide temperature therapy for said injured body member due to said increased thermal storage capacity provided by said phase change material, said gel material remaining pliable during said temperature therapy in order to facilitate said resilient support and said cushioning effect of said gel pad means, said phase change material being encapsulated in a sheet of capsules inside said gel pad means, said sheet of capsules preventing said phase change material from moving inside said gel pad means in order to provide a more uniform temperature distribution across said gel pad means; and
   means for removably securing said supporting means to said injured body member.

2. The orthopedic device of claim 1 wherein said gel pad means has first and second phase change materials having different melting temperatures.

3. The orthopedic device of claim 2 wherein said first phase change material includes means for providing hot temperature therapy and said second phase change material includes means for providing cold temperature therapy.

4. The orthopedic device of claim 3 wherein said second phase change material has a freezing temperature in the range of about 45 degrees Fahrenheit to about 55 degrees Fahrenheit, and said first phase change material has a melting temperature in the range of about 95 degrees Fahrenheit to about 125 degrees Fahrenheit.

5. The orthopedic device of claim 4 wherein said first phase change material has a heat of fusion in the range of about 30 cal/gm to about 65 cal/gm.

6. The orthopedic device of claim 1 wherein said device is an ankle brace.

7. The orthopedic device of claim 1 wherein said device is a walking brace.

8. The orthopedic device of claim 1 wherein said device is a knee brace.

9. The orthopedic device of claim 1 wherein said device is a wrist-forearm brace.

10. The orthopedic device of claim 1 wherein said sheet of capsules is located at one side of said gel pad means.

11. The orthopedic device of claim 10 wherein said phase change material is water.

12. The orthopedic device of claim 10 wherein said gel pad means has first and second phase change materials having different melting temperatures.

13. An orthopedic device for supporting an injured body member and providing temperature therapy to the member comprising:
    means for providing support to said injured body member;
    a gel pad adapted to be mounted between said supporting means and said injured body member in order to provide resilient support and cushioning effect for said injured body member, said gel pad including gel material and phase change material covered by a sheet of material, said phase change material providing increased thermal storage capacity to said gel material, said gel pad capable of being removed from between said supporting means and said injured body member so that the temperature of said gel pad may be changed, and then placed back between said supporting means and said injured body member in order to provide temperature therapy to said injured body member due to said increased thermal storage capacity of said phase change material, said gel material remaining pliable during said temperature therapy in order to facilitate said resilient support and said cushioning effect of said gel pad, said phase change material being encapsulated in a sheet of capsules inside said gel pad, said sheet of capsules preventing said phase change material from moving inside said gel pad in order to provide a more uniform temperature distribution across said gel pad; and
    means for removably securing said supporting means to said injured body member.

14. The orthopedic device of claim 13 wherein said phase change material is water.

15. The orthopedic device of claim 13 wherein said sheet of capsules is located at one side of said gel pad.

16. The orthopedic device of claim 13 wherein said gel pad has first and second phase change materials having different melting temperatures.

* * * * *